Figure 1:
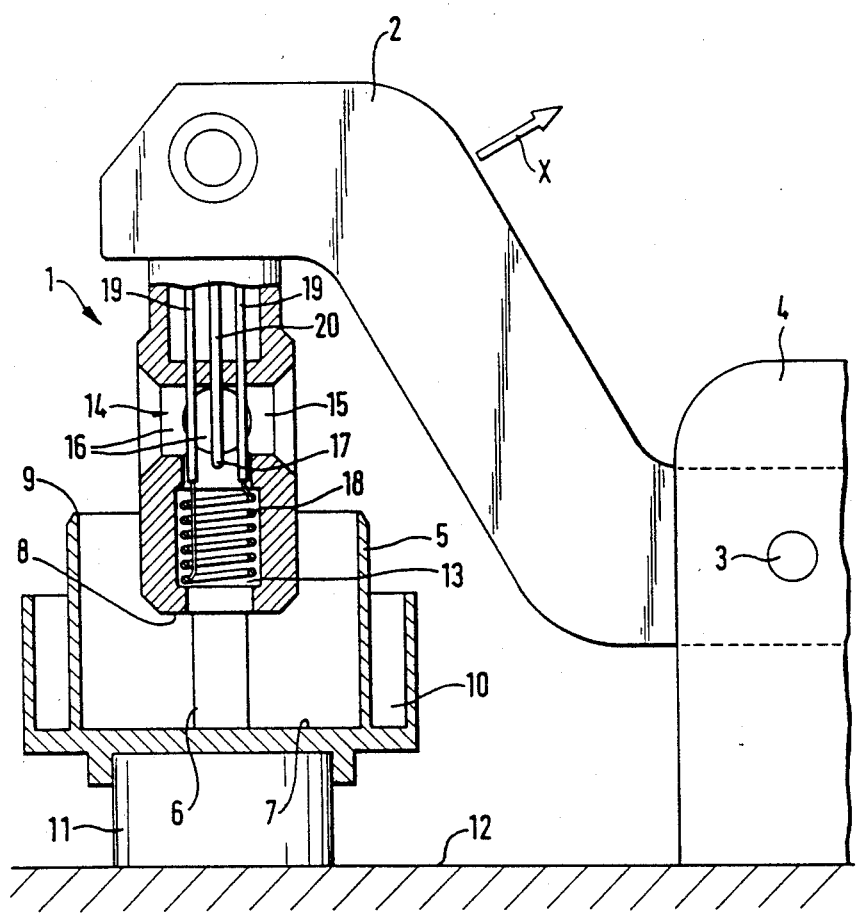

United States Patent [19]

Lohberg et al.

[11] Patent Number: 4,958,937

[45] Date of Patent: Sep. 25, 1990

[54] METHOD AND DEVICE FOR DETERMINING THE BOILING TEMPERATURE

[75] Inventors: Peter Lohberg, Friedrichsdorf; Arno May; Hans J. Krause, both of Goettingen; Dietmar Oberdorfer; Ulrich Plueguett, both of Goettingen, all of Fed. Rep. of Germany

[73] Assignee: Alfred Teves GmbH, Frankfurt Am Main, Fed. Rep. of Germany

[21] Appl. No.: 234,670

[22] Filed: Jul. 14, 1988

[51] Int. Cl.$^5$ ............................................. G01N 25/08
[52] U.S. Cl. ........................................ 374/16; 374/208
[58] Field of Search ............................... 374/16, 25–27, 374/208

[56] References Cited

U.S. PATENT DOCUMENTS

| | | | |
|---|---|---|---|
| 2,599,276 | 6/1952 | Norman | 374/16 |
| 2,832,219 | 4/1958 | Sapoff et al. | 374/16 |
| 3,119,250 | 1/1964 | Donnell | 374/27 |
| 3,263,487 | 8/1966 | Fiske, Jr. | 374/16 |
| 4,408,902 | 10/1983 | Peuker | 374/27 |

FOREIGN PATENT DOCUMENTS

| | | | |
|---|---|---|---|
| 223742 | 5/1987 | European Pat. Off. | 374/16 |
| 1598649 | 2/1972 | Fed. Rep. of Germany | 374/27 |
| 2655343 | 3/1978 | Fed. Rep. of Germany | 374/27 |
| 2721232 | 11/1978 | Fed. Rep. of Germany | 374/27 |
| 1260791 | 9/1986 | U.S.S.R. | 374/16 |

OTHER PUBLICATIONS

N.G. Aakalu et al., *IBM Technical Disclosure Bulletin*, "Float Type Boiling Point Sensor", vol. 13, No. 8, Jan., 1971, p. 2402.

*Primary Examiner*—William A. Cuchlinski, Jr.
*Assistant Examiner*—W. Morris Worth
*Attorney, Agent, or Firm*—Robert P. Seitter

[57] ABSTRACT

To determine the boiling temperature of a liquid, e.g. a hygroscopic brake fluid, a probe (1,1') is immersed partly, that is to say until an exactly predefined depth, into the test liquid. The probe (1,1') contains a measuring unit (14) which incorporates a temperature sensor (17) and which is in communication with the test liquid via a supply bore (13). The upper part of the measuring unit (14) forms a condensation zone (15) which is connected to the atmosphere via discharge openings (16). On ebullition of the test liquid, a bubbles or foam boiling zone (22) is formed directly on top of the surface (21) of the liquid, and on top of the zone (22) a condensation zone (15) is formed, out of which the condensate flows off to the outside. The temperature in the bubbles boiling zone is measured by means of the temperature sensor (17).

10 Claims, 5 Drawing Sheets

METHOD AND DEVICE FOR DETERMINING THE BOILING TEMPERATURE

The present invention relates to a method and a device for determining the boiling temperature of a liquid, such as a hygroscopic liquid, by means of a measuring unit containing a temperature sensor.

The determination of the boiling temperature is needed for instance for determining and monitoring the condition of a hygroscopic brake fluid for automotive vehicles. This is because due to the inevitable absorption of water, the boiling point drops in the course of time so far as to endanger the brakes' function. This aging is dependent on many parameters, for what reason the fluid's age alone does not permit to draw conclusions in respect of the boiling point and thus on the usability of the brake fluid.

According to a German industry standard, a method is known already which permits to determine the boiling point of a brake fluid with a precision of roughly 3 to 5 K. This method necessitates the provision of special laboratory equipment and trained operating personnel therefor. Moreover, the determination of the boiling point by this method takes about 20 minutes, i.e. it is time-consuming. Therefore, this method is inappropriate for series measurements in workshops for automotive vehicles.

A method and a device for the determination of the boiling point of a brake fluid is known already from European patent specification 56 424, wherein the brake fluid is heated and the temperature change of the heater as a function of time is measured. To this end, a probe with a hollow chamber containing a heater and a temperature sensor is immersed completely into the brake fluid. The hollow chamber has an opening for the inlet of the brake fluid. Connected to the probe is an electronic display and evaluation system by which a variation of the temperature change as a function of time is to be recorded and to be evaluated as a unit for the boiling point of the brake fluid. The upper part of the hollow chamber is gastight and comprises a venting arrangement which is shut off after the immersion of the probe and the escape of the air.

According to a similar method which is described in European patent specification 74 415, likewise a probe composed of a heater and a temperature sensor is immersed completely into the test liquid. After the heater has been activated, the liquid evaporates, while it is to be ensured that the gas bubbles evolving rise along the heater. The constant temperature of the heater resulting from the formation of the gas bubbles is measured by means of the temperature sensor and serves as a measure for the boiling point of the liquid.

It is doubtful whether any one of the methods disclosed in the two above-mentioned European patents actually enables to determine the boiling point of a brake fluid to sufficient precision. This is because it is not the boiling temperature that is measured by both methods, but directly or indirectly the temperature of the heater. However, as is common knowledge, there is no connection between the temperature of the heater and the boiling temperature. To initiate the ebullition, the heater must be heated up in any case to an excess temperature, the magnitude of which depends on various parameters. Maybe an exact calibration, a limitation to a specific liquid and strict preservation of the boundary conditions such as the heat-up speed, permit to determine a mean excess temperature, on attainment of which ebullition occurs and on the basis of which a rough distinction between two or three boiling temperature zones can be performed. A like measurement would be too inexact for practical applications though.

It is therefore an object of the present invention to overcome the described disadvantages of known methods and devices and to provide a method for the determination of the boiling temperature of a liquid, e.g. a hygroscopic brake fluid which allows a comparatively exact determination of the boiling point and which can be performed by a simple apparatus easy to operate. Besides, the result of the measurement should be obtained in a shortest possible time. Even an unskilled person should be in a position to attend to the apparatus.

It has been proven now that this object can be achieved in a technically advanced manner by a method of the type initially referred to, the special characteristics of which reside in that the measuring unit is designed such and is arranged such in relation to the liquid to be tested that, on boiling of the liquid, a bubbles boiling zone or foam boiling zone, respectively, is formed on the liquid surface and, on top thereof, a condensation zone is formed, in that the condensed liquid flows off from the condensation zone, in that atmospheric pressure is prevailing in the measuring unit, and in that the temperature in the boiling zone is measured directly above the liquid level, that is the surface of the liquid to be tested.

A device for implementing this method is furnished with a probe containing a measuring unit with a temperature sensor and inventively consists in that the probe can be immersed partly, namely until a predefined depth, into the liquid to be tested and that it contains a supply opening through which liquid enters the measuring unit and forms a liquid level directly beneath the temperature sensor, as well as in that there is a condensation zone in the measuring unit above the zone in which the boiling temperature can be measured, which condensation zone is connected with the atmosphere via discharge openings for the condensate.

The instant invention is based on the recognition that actually the temperature of the boiling liquid must be determined for obtaining a sufficiently exact result of measurement. It makes use of the knowledge that, with the atmospheric pressure prevailing, the boiling temperature is identical with the steam saturation temperature. This knowledge implies at the same time that the steam condenses already in the event of a very small decline in temperature. Steam saturation temperature prevails inside of steam bubbles. To prevent the steam bubbles from condensing on their way to the liquid surface, any location in the liquid penetrated by them must have a temperature which is higher than the steam saturation temperature. Therefore, according to this invention, measurement is effected in a bubbles boiling zone or foam boiling zone, respectively, which is formed directly above the liquid surface, that is the liquid level, and in which atmospheric pressure is prevailing. Above this boiling zone, the boiling bubbles are deprived of so much heat that they condense. The condensate is discharged so that it will not return to the zone of measurement, namely the boiling zone, and destroy the balance in the boiling zone and adulterate the measurement.

The device according to this invention serves to so-to-speak spatially separate a quantum of the turbulently boiling liquid from a larger total volume of the same liquid, with the local heat distribution being optional, without interrupting the quantum's connection to the total volume. When the probe is immersed until a specific depth into the liquid to be tested, a liquid surface or liquid level is formed in the measuring unit which assumes a permanently equally defined relative position to the measuring unit and, more particularly, to the temperature sensor. The sensor does not immerse into the liquid, but only into the bubbles or foam boiling zone, respectively.

According to a favourable embodiment of the inventive method, liquid out of a container, e.g. a test liquid receptacle, is supplied to the measuring unit during boiling, a balance being established between the evaporation, i.e. the formation of boiling bubbles or boiling foam, the condensation, the discharge of the condensate and the replenishment of fresh liquid into the probe and thus into the measuring unit.

It is a special advantage if the measuring unit including the temperature sensor is preheated by heat transfer from the test liquid and/or the boiling bubbles to such an extent as to establish the balance in the measuring unit between the delivery and discharge of the liquid, the formation of boiling bubbles and the condensation. Expediently, the heat capacity of the temperature probe is conformed to the mass of the bubbles foam such that the heat energy of the liquid bodies of the steam bubbles which collapse during condensing suffices to heat up the temperature probe when it is moistened with a heat flow that is constant in its mean value to such effect that the temperature of the steam bubbles' contents is measured without any additional deprivation of heat. Since atmospheric pressure prevails in this area, this measured temperature is identical with the boiling temperature of the test liquid.

According to a favourable design of the inventive device, the probe can be immersed vertically into the liquid, and the supply opening of the probe is designed in the form of a supply bore which is open at the probe's immersed end face and which delivers liquid vertically upwardly to the measuring unit.

According to another embodiment of the inventive device, in the operating condition, the supply opening, the measuring unit and the condensation zone are arranged vertically on top of one another.

Suitably, the supply opening or supply bore incorporates a heater coil which serves to heat up the liquid disposed in this area until it boils turbulently.

According to another embodiment, the probe is disposed at a tiltable arm extending wherethrough are electric junction wires, for instance for the temperature sensor, for the heater coil etc.

In order to adjust the defined relative position of the liquid surface, i.e. the liquid level, in the interior of the measuring unit, the test liquid is expediently filled into a receptacle, the filling height of which is determined e.g. by overflow openings or overflow edges, and the depth of immersion of the probe into this receptacle and thus into the liquid is predetermined by range spacers, for example by a support mounted on the receptacle's bottom or a level-defining stop on which the probe can be seated.

Further, it is arranged for according to an embodiment of this invention to return the condensate from the condensation zone through the discharge openings into the receptacle.

Another embodiment of the inventive device resides in that the probe is arranged as an element floatable on the test liquid and immersing into the liquid just so far that the temperature sensor will measure the temperature in the bubbles and foam boiling zone when the liquid is boiling.

Besides, it is provided by the invention to equip the device with a preheating device allowing to heat up the probe completely or partly, above all the temperature sensor and/or the condensation zone of the measuring unit, to a temperature near the boiling temperature of the test liquids.

Owing to the preheating, the measuring apparatus lends itself to use even at low outside temperatures, without there being the risk of a too fast condensation of the boiling bubbles in the condensation zone and thus of a disturbed balance between the formation of boiling bubbles, the condensation and the replenishment of fresh liquid into the measuring unit. Besides, there will be avoided a too long heating of the test liquid filled into the test liquid receptacle and hence a 'boiling out' of the test liquid what might impair the accuracy of measurement.

According to another favourable embodiment, a circuit configuration for controlling the method and the device of this invention disposes of a sequence control which controls a current source for the supply of a liquid heating device, electronic circuitries for the amplification and the processing of a test signal produced by means of a temperature sensor, as well as an indicator.

Additionally, a like circuit configuration can comprise a boiling level detector which can be supplied with the possibly processed output signal of the temperature sensor and which produces a comparison signal rising with time delay relative to the commencement of the measuring action or the switching-on of the heating, which comparison signal is compared with the output signal of the temperature sensor and which permits to recognize the beginning of the boiling phase. To this end, expediently, the coincidence of the output signal of the temperature sensor with the comparison signal can be rated as criterion for the beginning of the boiling phase and results in the indication of the boiling temperature as well as the termination of the measuring action.

Further features, advantages and possibilities of application of this invention can be gathered from the following description of embodiments by way of the accompanying drawings.

Figure 2:
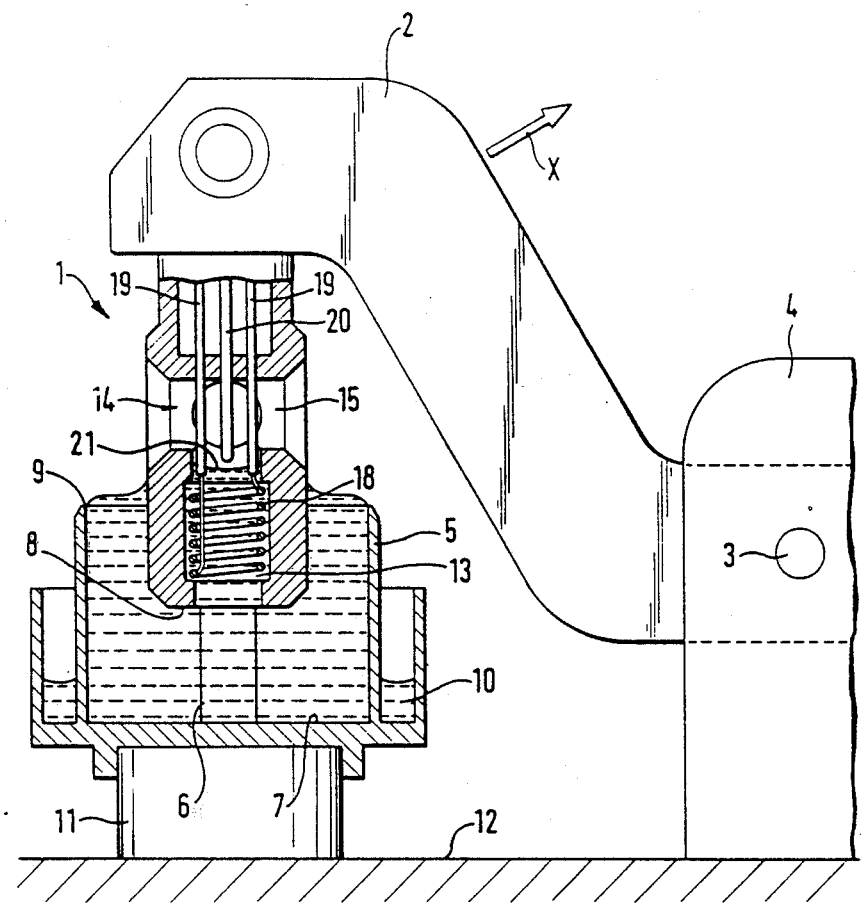
Figure 3:
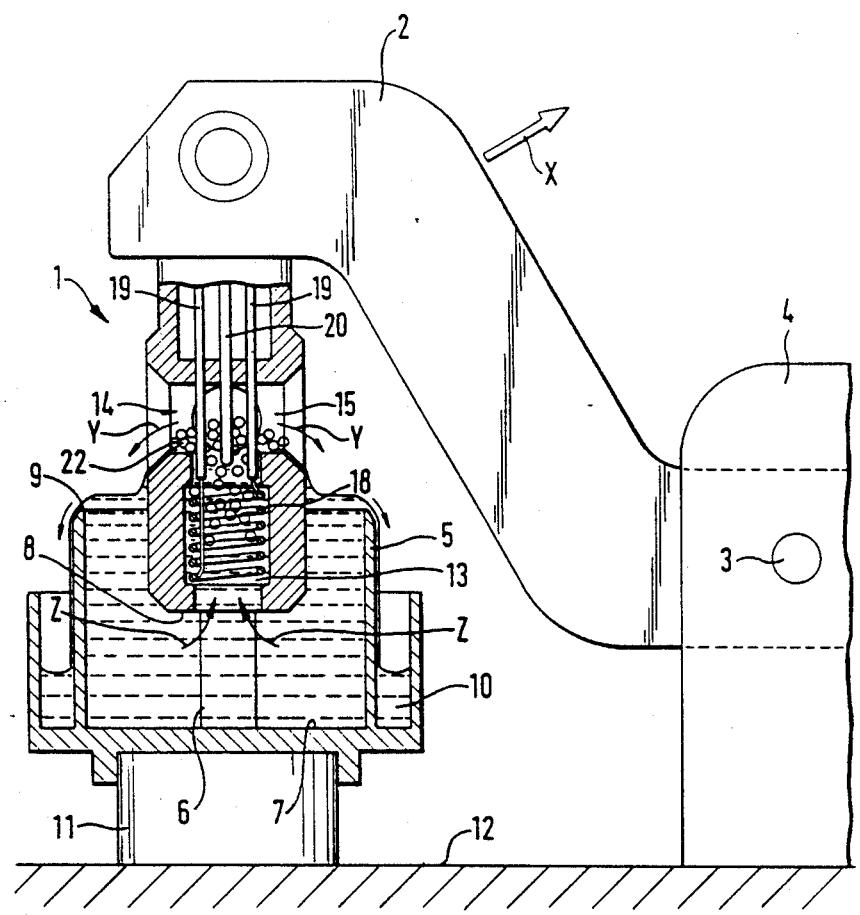
Figure 4:
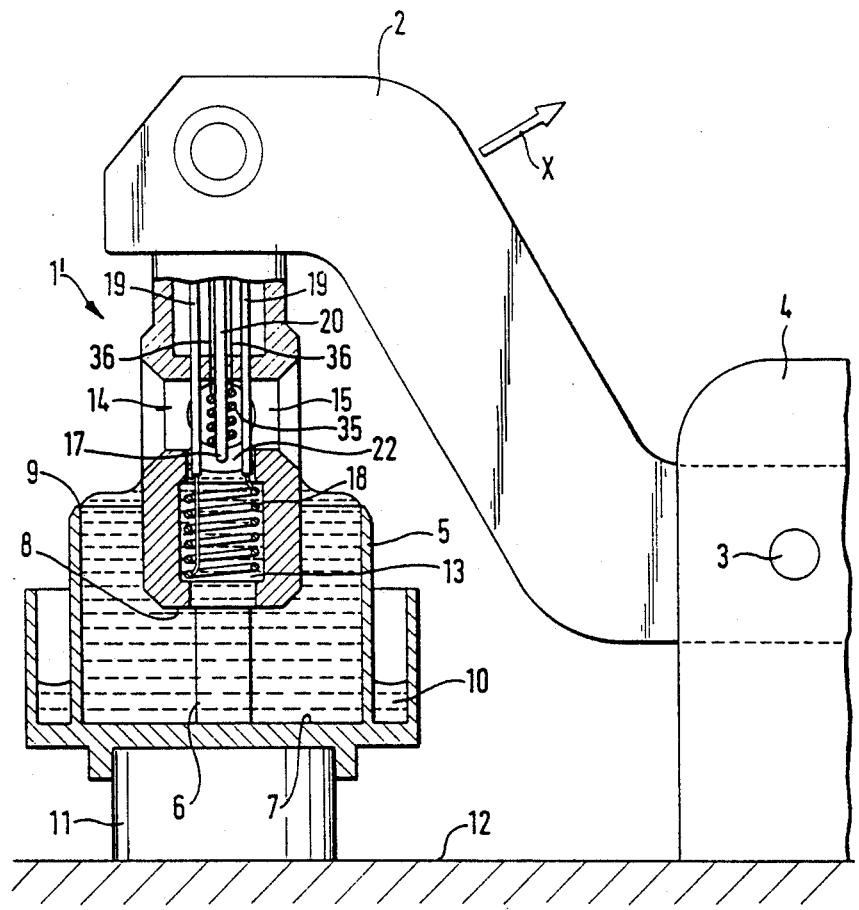
Figure 5:
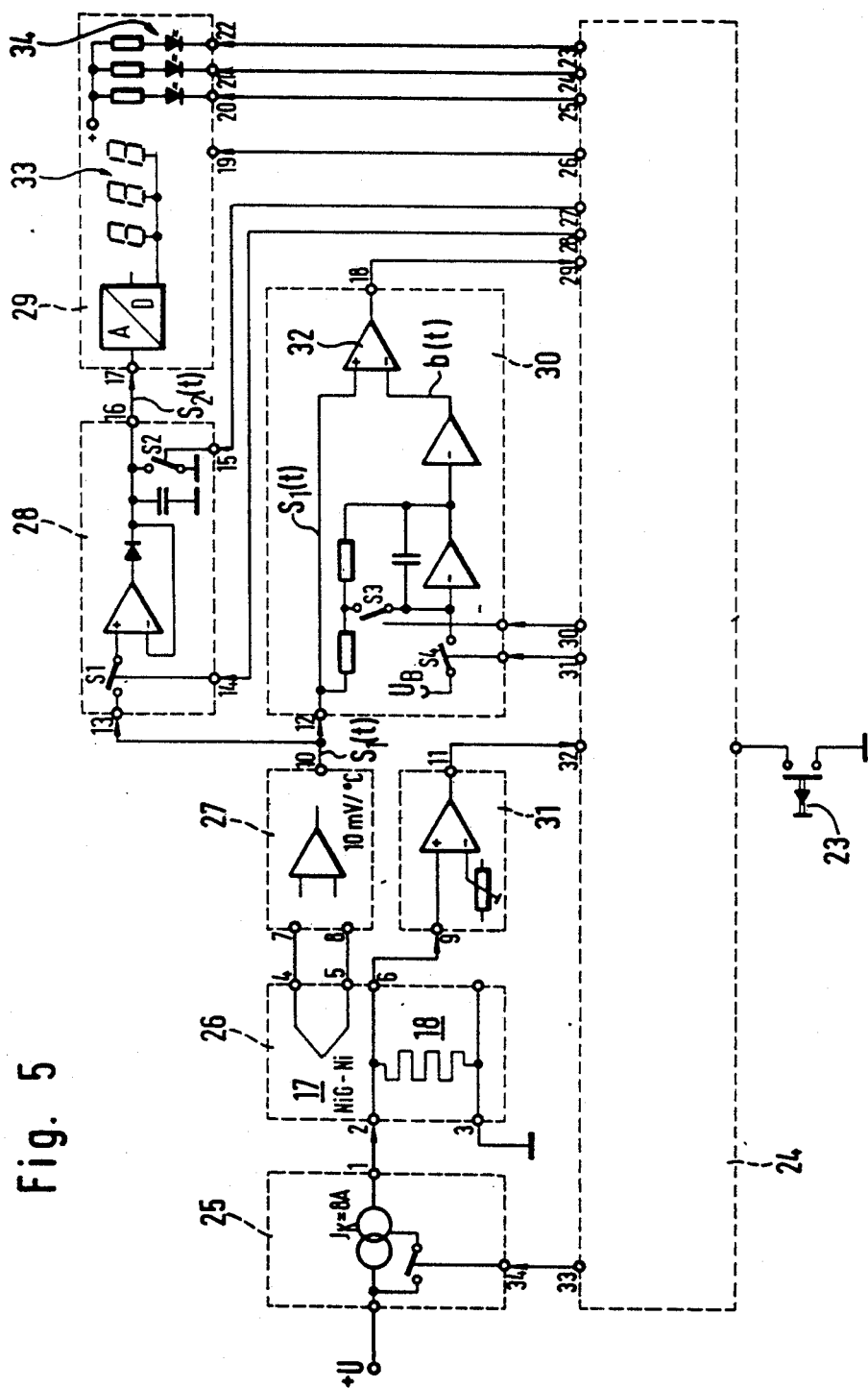

In the drawings,

FIG. 1 is, in a simplified view and partially in vertical cross-section, a probe according to an embodiment of this invention which is fitted to a tiltable arm and which is swivelled into a still empty test liquid receptacle, FIG. 2 is the embodiment according to FIG. 1, in the same illustration like FIG. 1, on a reduced scale though, after the immersion of the probe into the test liquid, and namely prior to the beginning of ebullition, FIG. 3 is the embodiment according to FIGS. 1 and 2 in the same way of illustration like FIG. 2, however, after the beginning of ebullition, FIG. 4 is, alike the illustration of FIG. 2, another embodiment of the instant invention, namely a probe furnished with a preheating device, and FIG. 5 is, in a block diagram a circuit configuration for implementing the method by means of the probes according to FIGS. 1 to 4.

As is shown in FIG. 1, a probe 1 of the inventive type is secured to a tiltable arm 2 which is rotatably supported on a shaft 3 of a brake-fluid test device 4. This test device which is but hinted at incorporates among others an electronic circuitry (FIG. 4) for sequence control and evaluation of the test signals, a power-supply unit for the current supply of the sequence control and for heating up the test liquid, indicator lamps indicating the readiness for use of the device or malfunctions as well as a screen for display of the measurement or test results, respectively. These components which are standard use in devices of this type are not illustrated.

FIG. 1 shows the operating position of the probe 1. The probe 1 projects vertically into a test liquid receptacle 5. The depth of immersion into the liquid or into the receptacle 5, respectively, is determined by a level-defining stop 6 which, for instance, is composed of several pins mounted on the receptacle's bottom 7, on which the probe 1 is abutting with its end face 8. On top, the receptacle 5 ends with an overflow edge 9, beyond which—when the probe 1 is immersed into the receptacle 5 filled already—the liquid displaced may get into an overflow chamber 10 at the periphery of the receptacle 5.

A measuring cup support 11 ensures the alignment of the receptacle 5 in relation to the tiltable arm 2 and ensures also a safe retention of the receptacle 5. Expediently, said support 11 is secured to a base plate 12 connected to the test device 4.

In the probe 1, there are disposed vertically on top of one another a supply bore 13 which is open at the end face 8 of the probe 1 projecting into the receptacle 5, as well as a measuring unit 14 extending to which is the supply bore 13 and the upper part of which forms a condensation zone 15. This measuring unit 14 is open to atmosphere through vertical discharge openings or bores 16 at the level of the condensation zone 15.

Protruding into the measuring unit 14 is a temperature sensor 17 which, for instance, is made of a thermocouple element whose sensing zone is on top of the sensor protruding into the measuring unit.

Alike an immersion heater, a heater coil 18 is accommodated in the supply bore 13 which is supplied with current via junction wires 19 extending through the measuring unit 14. Said junction wires 19 as well as junction wires 20 for the temperature sensor 17 extend through the tiltable arm 2 to the test device 4—which cannot be seen from the illustration.

FIG. 2 illustrates the filling condition of the test liquid receptacle 5 and that of the probe 1 prior to the commencement of measuring and, respectively, prior to switching on of the heater coil 18. To accomplish this filling condition, first the probe 1 was taken out of the receptacle 5 by swivelling the arm 2 in the direction of the arrow 21, then the test liquid receptacle 5 was brimmed and was positioned on the support 11. Subsequently, the probe 1 was swivelled back to its illustrated position. The liquid which was displaced on immersion of the probe 1 moved into the overflow chamber 10. Through the supply bore 13, the liquid level 21 rose as far as until attainment of the relative spatial position between the liquid level and the temperature sensor 17, which position is of vital importance for the invention. The distance between the peak of the temperature sensor 17 and the liquid surface amounts to 1 to 1.5 mms, for instance. The liquid level 21 adopted the curved shape shown in FIG. 2 due to adhesion of the liquid at the wall in the interior of the supply bore 13, the diameter of which amounts to roughly 6 mms at the boundary surface to the measuring unit in the embodiment on which the illustration is based.

FIG. 3 depicts what is happening in the measuring unit after ebullition has commenced. The boiling bubbles produced in the vicinity of the heater coil 18 rise upwards and form a bubbles foam above the liquid level 21 in the bubbles boiling zone 22, which foam rises beyond the liquid surface and fills the area in which the temperature sensor 17 is disposed. Above the bubbles foam, namely in the condensation zone 15, the bubbles will dissolve. The condensate flows through the discharge bores 16 in the direction of the arrows 23 back into the receptacle 5 or into the overflow chamber 10. Through the supply bore 13, fresh liquid flows out of the receptacle 5 in the direction of the measuring unit 14, as is shown by the arrows 24. By virtue of convection, boiling bubbles are permanently supplied to the bubbles boiling zone 22.

The probe 1' according to FIG. 4 differs from the probe 1 described by way of FIGS. 1 to 3 solely by the provision of a preheating device which was realised by a heater coil 35 in this embodiment. Said heater coil 35 was wound around the temperature sensor 17 and is realised by electric junction wires 36 which likewise extend through the tiltable arm 2 to the test device 4.

The preheating device 35, 36 preheats the measuring unit, in particular the temperature sensor 17 and the preheating zone 15, to a temperature close to the boiling temperature of the test liquid. This can be realised suitably by a short-time supply of current to the heater coil 35 prior to the commencement of the measuring action itself. As a result of the electric heating-up by means of the heater coil 35, the thermal energy taken from the heated liquid and/or the boiling bubbles becomes relatively small, which has favourable effects on establishing and maintaining the state of balance between the formation of boiling bubbles, the condensation and the supply of the fresh liquid. This also promotes the stability of the state of balance even when temperature sensors with a relatively large thermal mass are used. The heating-up action of the liquid and thus the time required for the measurement can be reduced by preheating.

FIG. 5 displays the structure of an electric circuitry for the operation of the brake fluid test device 4 and for the control of the measuring action, respectively.

A measuring action is started by means of a start push button 23. The sequence of the individual functions, the switching on and off of various electric function units shown in FIG. 5, the display of the operating condition of the test device 4 and of the result of measurement is controlled by an integrated circuit, namely by the sequence control 24. For heating up the test liquid, that is the quantity of liquid prevailing in the supply bore 13, by means of the heater coil 18, there is provision of a constant current source 25. The temperature sensor 17, for instance a NiCr-Ni thermocouple element, and the heater coil 18 are comprised in one block 26 in FIG. 5. The output signal of the thermocouple element 17 is processed by means of a test amplifier 27. The output signal $S_1(t)$ of the amplifier 27 is supplied to a peak voltmeter 28. The output of this voltmeter 28 leads to an indicator 29.

For detection of the boiling phase, there is still provision of a boiling level detector 30. A temperature monitor 31 serves to monitor the temperature in the measuring unit and to detect an excess temperature.

After the test liquid receptacle 5 has been filled and the probe 1 has been swivelled thereinto, depression of the push button 23 will activate the constant current source 25 and thereby switch on the heating 18. Simultaneously, the voltage output signal of the temperature sensor 17 is supplied to the test amplifier 27, and its output signal $S_1(t)$ is evaluated two times. On the one hand, it is compared with a signal b(t) produced within the boiling level detector and serving to quickly recognize the boiling phases. To this end, a comparison signal b(t) commencing with time delay and rising ramp-like against time, i.e. a reference voltage, will be produced within the boiling level detector 30 after the onset of the heating-up action. The time lag and the steepness of the rising signal b(t) are chosen such that in all cases occurring in practice, starting from any desired pre-temperature of the test liquid, the test signal voltage $S_1(t)$ at the output of the amplifier 27 will reach the boiling level before the reference voltage b(t) does.

Since the temperature test signal $S_1(t)$ remains practically constant after the boiling temperature has been reached and the time lag of the comparison signal b(t) was effective during the heating-up phase, after the beginning of the boiling phase—provided there is no technical malfunction—the reference voltage b(t) will approach with time lag the test signal, i.e. the test voltage $S_1(t)$, and will finally reach the level of the signal voltage a short time later. This equal voltage is detected by a comparator 32 in the interior of the boiling level detector 30 and evaluated as criterion for the attainment of the boiling phase. If this equal voltage will not occur after a defined maximum period of time, this indicates an error. In a like case, the measuring action will be terminated by the sequence control, and the error will be displayed.

On the other hand, that means beside the analysis in the detector 30 for recognizing the boiling phase, the output signal $S_1(t)$ is supplied to the voltmeter 28 and serves for the determination of the boiling temperature. This is effected by a measurement of the peak voltage in the voltmeter 28 and by transformation and indication of the output signal $S_2(t)$ of this voltmeter 28 by means of the three-digit display panel 33 of the indicator 29. The symbolically illustrated varicoloured light-emitting diodes 34 within the indicator 29 signal the readiness for use, the performance of a measuring action or the occurrence of an error by the corresponding diode lighting up.

Hence follows that, by virtue of the boiling level detector 30, the attainment of the boiling phase is quickly recognized, the indication and the storing of the indication of the boiling temperature is initiated and the heating-up action of the test liquid is terminated. This avoids that the test liquid is heated up unnecessarily long and that thereby the water is removed from the test liquid by boiling and that the test value is adulterated.

Besides, the boiling level detector 30 can be made use of for controlling the preheating device—see FIG. 4 and the pertinent explanation. For this purpose, the preheating device is activated when the temperature sensor 17 signals that a minimum test liquid temperature is decreased at the point of time of the onset of sequence control.

On the other hand, it is also possible to determine and to control the preheating temperature by measuring the electrical resistance of the heater coil 35. Another embodiment of this invention resides in that each measuring action is principally preceded by a short preheating phase. The amount of the temperature reached by preheating is of subordinate significance because in the subsequent measuring action the temperature required for bringing about the balance will automatically adjust by heat transfer from the boiling bubbles onto the temperature sensor or by cooling due to the condensing boiling bubbles.

We claim:

1. A device for determining the boiling temperature of a test liquid comprising a probe and measuring means, said probe including a measuring unit with a temperature sensor, the probe being immersible in said test liquid to a predetermined depth, means for supporting said probe to maintain said predetermined depth of said probe in said liquid, said probe including a supply opening through which liquid enters the measuring unit and forms a liquid level directly beneath the temperature sensor, means in thermal contact with said test liquid for heating said test liquid to a boiling temperature to cause ebullition of said test liquid in a boiling zone on top of said liquid level, in which the boiling temperature is detected by said temperature sensor a condensation zone in the measuring unit in which condensate forms above the boiling zone, said condensation zone being connected with the atmosphere by way of discharge openings for the condensate, wherein the heating means is inserted into the supply opening and wherein the probe is arranged on a tiltable arm extending through which are electric junction wires for the temperature sensor and for the heating means.

2. A device for determining the boiling temperature of a test liquid comprising a probe and measuring means, said probe including a measuring unit with a temperature sensor, the probe being immersible in said test liquid to a predetermined depth, said probe including a supply opening through which liquid enters the measuring unit and forms a liquid level directly beneath the temperature sensor, means for heating said test liquid to a boiling temperature to cause ebullition of said test liquid in a boiling zone on top of said liquid level, in which the boiling temperature is detected by said temperature sensor a condensation zone in the measuring unit in which condensate forms above the boiling zone, said condensation zone being connected with the atmosphere by way of discharge openings for the condensate, wherein the test liquid is contained in a receptacle having a predefined filling height, and the depth of immersion of the probe into this receptacle, that is into the liquid, is predetermined by a support mounted on the receptacle's bottom or a level-defining stop on which the probe can be seated.

3. A device as claimed in claim 2, wherein the filling height of the receptacle is determined by overflow edges of said receptacle.

4. A device as claimed in claim 2, wherein the condensate is returned from the condensation zone through the discharge openings into the receptacle.

5. A device for determining the boiling temperature of a test liquid comprising a probe and measuring means, said probe including a measuring unit with a temperature sensor, the probe being immersible in said test liquid to a predetermined depth, said probe including a supply opening through which liquid enters the measuring unit and forms a liquid level directly beneath the temperature sensor, means for heating said test liquid to a boiling temperature to cause ebullition of said test liquid in a boiling zone on top of said liquid level, in which the boiling temperature is detected by said temperature sensor a condensation zone in the measuring unit in which condensate forms above the boiling zone, said condensation zone being connected with the atmosphere by way of discharge openings for the condensate, and said device provided with preheating means for heating the probe to a temperature near the boiling temperature of the test liquid.

6. A device as claimed in claim 5, wherein the preheating means heats up the measuring unit, in particular the temperature sensor in the condensation zone.

7. A device as claimed in claim 5, wherein the preheating means is provided in the form of a heater coil which along with said temperature sensor projects through the condensation zone and into the boiling bubbles zone.

8. A device for determining the boiling temperature of a test liquid comprising a probe and measuring means, said probe including a measuring unit with a temperature sensor, the probe being immersible in said test liquid to a predetermined depth, means for supporting said probe to maintain said predetermined depth of said probe in said liquid, said probe including a supply opening through which liquid enters the measuring unit and forms a liquid level directly beneath the temperature sensor, means provided in thermal contact with said test liquid for heating said test liquid to a boiling temperature to cause ebullition of said test liquid in a boiling zone on top of said liquid level in which the boiling temperature is detected by said temperature sensor, a condensation zone in the measuring unit in which condensate forms above the boiling zone, said condensation zone being connected with the atmosphere by way of discharge openings for the condensate, and including a circuit configuration for controlling said heating means, said circuit configuration including a sequence control which controls a current source for current supply of said heating means, electronic circuits for the amplification and the processing of a test signal produced of said temperature sensor and an indicator means which indicates the boiling temperature.

9. A device and circuit configuration as claimed in claim 8, wherein a boiling level detector which is supplied with a processed output signal of the temperature sensor and which produces a comparison signal b(t) rising with time delay relative to the commencement of the switching-on of the heating device, which comparison signal is compared with said output signal of the temperature sensor to manifest the beginning of a boiling phase.

10. A device and circuit configuration as claimed in claim 8, wherein the coincidence of an output signal of the temperature sensor with the comparison signal b(t) produced in a boiling level detector provides a criterion for the beginning of a boiling phase and thereby the indicator means results in an indication of the boiling temperature and the termination of measuring action.

* * * * *